United States Patent [19]
Pratt et al.

[11] Patent Number: 5,893,862
[45] Date of Patent: Apr. 13, 1999

[54] SURGICAL APPARATUS

[76] Inventors: Arthur William Pratt, 5320 Montiverdi Place, West Vancouver, Canada, V7W 2W8; Ian McDougall, 449 East 16th Street, North Vancouver, Canada, V7L 2T4

[21] Appl. No.: 08/843,606

[22] Filed: Apr. 10, 1997

[51] Int. Cl.$^6$ .................................................. A61B 17/32
[52] U.S. Cl. ........................................ 606/170; 604/22
[58] Field of Search ............................ 606/1, 83, 167, 606/170, 171, 180; 604/22

[56] References Cited

U.S. PATENT DOCUMENTS

| | | |
|---|---|---|
| 2,850,007 | 9/1958 | Lingley . |
| 3,732,858 | 5/1973 | Banko . |
| 3,776,238 | 12/1973 | Peyman et al. . |
| 3,844,272 | 10/1974 | Banko . |
| 3,893,445 | 7/1975 | Hofsess . |
| 3,996,935 | 12/1976 | Banko . |
| 4,041,947 | 8/1977 | Weiss . |
| 4,282,884 | 8/1981 | Boebel . |
| 4,308,875 | 1/1982 | Young . |
| 4,320,761 | 3/1982 | Haddad . |
| 4,368,734 | 1/1983 | Banko . |
| 4,530,356 | 7/1985 | Helfgott et al. . |
| 4,538,611 | 9/1985 | Kelman . |
| 4,570,632 | 2/1986 | Woods . |
| 4,577,629 | 3/1986 | Martinez . |
| 4,590,935 | 5/1986 | Ranalli . |
| 4,662,869 | 5/1987 | Wright . |
| 4,834,729 | 5/1989 | Sjostrom .................... 604/22 |
| 4,884,569 | 12/1989 | Fedorov et al. . |
| 4,900,300 | 2/1990 | Lee . |
| 5,024,652 | 6/1991 | Dumenek et al. . |
| 5,047,008 | 9/1991 | de Juan, Jr. et al. . |
| 5,057,098 | 10/1991 | Zelman . |
| 5,290,303 | 3/1994 | Pingleton et al. ............. 606/170 |
| 5,391,177 | 2/1995 | Schwartz . |
| 5,403,334 | 4/1995 | Evans et al. ................. 606/159 |
| 5,618,306 | 4/1997 | Roth et al. . |

FOREIGN PATENT DOCUMENTS

| | | |
|---|---|---|
| WO9301757 | 2/1993 | WIPO . |
| WO9624298 | 8/1996 | WIPO . |

OTHER PUBLICATIONS

Blumenthal: Manual ECCE, the Present State of the Art; Klinische Monatsblatter Für Augenheilkunde 1994; 205:266–270.

McIntyre, DJ: Phacosection Cataract Surgery. In Steinert, R.F., Fine, I.H., Gimbel, H.V et al., (FDS) Cataract Surgery, Techniques, Complications and Management: Philadelphia: WB Saunders 1995: 119–123.

Kansas P: Phaco Fracture in Cataract Surgery, Alternative Small Incision Techniques by Rozakis (ED) Slack 1990: 45–69.

Khouri E: Manual Phacofragmentation, Manual Meeting of Canadian Opthalmological Society; Jun. 2, 1996 Ottawa. (This was an oral presentation, no printed document exists as yet).

Vaughan D, Cook R and Asbury T: General Ophthalmology: Lange Medical Publications, 1968.

Tipperman R, et al: Clinical Update: Cataract The American Academy of Ophthalmology, 1996 Preferred Practice Pattern: Cataract in the Adult Eye: The American Academy of Ophthalmology, 1996.

*Primary Examiner*—William Lewis
*Attorney, Agent, or Firm*—Christie, Parker & Hale, LLP

[57] ABSTRACT

Apparatus to remove tissue. The apparatus has an outer cannula and an inner cannula received within the outer cannula. The cannula are longitudinally movable relative to each other. There is an abutment at the end of one cannula to contact the other cannula. A drive permits advancing of the other cannula to contact the abutment whereby tissue between the other cannula and the abutment is removed. The invention finds particular application in removable of lens tissue from the eye of a human or other animal.

18 Claims, 8 Drawing Sheets

SURGICAL APPARATUS

FIELD OF THE INVENTION

The present invention relates to an apparatus to remove tissue from body parts through a small incision. Its main application is to remove and extract lens tissue from the eye of a human or other animal.

DESCRIPTION OF RELATED ART

The normal lens of an eye is a biconvex, avascular, colourless and almost completely transparent structure. It is about 5 mm thick and 9 mm in diameter. The lens is suspended behind the iris by the zonular fibers which connect it with the ciliary body. Anterior to the lens is the aqueous humour; posterior to it the vitreous humour. The lens capsule is a semi-permeable membrane. A subcapsular epithelium is present anteriorly. The nucleus and cortex are made up of long concentric lamellas. The nucleus is harder than the surrounding cortex. With age, subepithelial lamellar fibers are continuously produced so that the lens gradually becomes larger and less elastic throughout life.

In childhood and youth the lens has a semi fluidic consistency which permits its aspiration through a small bore cannula and small incision. In the adult eye, progressive hardening of the nucleus prevents aspiration of the nuclear tissue.

The sole function of the lens is to transmit and focus light rays upon the retina. It accomplishes this by being translucent and able to refract light. A cataract is a lens opacity. Cataracts vary markedly in degree of density, size and location. The cataract may be due to a variety of causes but usually cataracts are associated with aging. Some degree of cataract formation is to be expected in persons over age 70. Most are bilateral though rate of progression is seldom equal. Traumatic cataracts and congenital cataracts are less common and other types are rare.

Cataractous lenses are characterized by protein alteration, lens edema, necrosis and disruption of the normal continuity of the lens fibers. In general, the lens edema varies directly with the stage of cataract development. The immature (incipient) cataract is only slightly opaque. A completely opaque, mature (moderately advanced) cataractous lens is somewhat edematous. When the water content is maximal and the lens capsule is stretched, the cataract is called intumescent (swollen). In a hypermature (far advanced) cataract, water has escaped from the lens leaving a relatively dehydrated, very opaque lens and a wrinkled capsule.

Senile cataract is by far the most common type of cataract. In this type, the conversion of soluble low-molecular weight cytoplastic proteins to insoluble high-molecular weight aggregates, which are insoluble phases, and insoluble membrane protein matrices are major mechanisms contributing to the hardening of the nucleus and the loss of transparency of the lens.

Progressively blurred vision is the principal symptom. Glaucoma and lens induced uveitis may develop as complications of cataract formation.

There is no medical treatment for cataract.

The need for cataract surgery is indicated when visual impairment interferes with normal activities or if glaucoma or lens induced uveitis develop as complications of the cataract.

A number of techniques have been and are being used to remove the cloudy, cataractous lens or to provide a clear path for the transmission of light to the retina.

Of largely historical interest is the ancient procedure of couching in which an instrument entered the eye through an incision in the peripheral cornea and was used to push and dislocate the entire lens posteriorly into the vitreous humour, off the visual axis, to restore a clear path to the retina for the light.

In more recent times, there are two principal types of cataract surgery, intracapsular and extracapsular. The former consists of the removal of the lens in toto i.e. within its capsule. In the extracapsular operation a portion of the anterior capsule is opened and removed. Subsequently, the nucleus and cortex are also removed by various means leaving the peripheral portion of the anterior capsule and the posterior capsule behind.

In the intracapsular technique, a large incision is made at the limbus or the peripheral cornea and the cornea retracted. Purchase is obtained on the anterior lens capsule with special lens capsule forceps, or by a suction apparatus, called a erysiphake, or by freezing the small tip of an instrument called a cryophake. The entire lens is pulled from the eye and the corneal wound sutured. With the removal of the lens a major focusing component of the eye has gone and needs replacement in the form of a spectacle lens, a corneal contact lens, or an implantation of an intraocular lens at the time of the cataract extraction.

Extracapsular cataract surgery is performed with a standard single incision 10 mm or greater in length at the limbus. Extracapsular cataract extraction, in its early form was accomplished by making a larger (>11 mm) incision into the anterior chamber, tearing an opening through the anterior capsule of the lens, and expressing the nucleus by applying pressure near the posterior edge of the wound and counter pressure at the opposite limbus. As much as possible of the remaining cortex was irrigated from the eye and the incision closed with sutures.

The advent of the operating microscope permitted the development of the modern extracapsular cataract surgical techniques which feature a more precise and controlled opening of the anterior capsule and precise and complete removal of the cortical material left after the nucleus expression. The removal is done with devices that offer irrigation, which maintains the volume of the anterior chamber, and aspiration, which removes the cortex by suction, usually through small gauge cannulas.

Recently, several techniques have been developed to allow manual nucleus expression or manual extraction to be performed through a smaller incision than had been used previously. A small incision is desirable because it causes less astigmatic effect or alteration in corneal curvature, heals faster, is stronger and is generally more stable than a larger incision. Whereas traditional manual nucleus expression uses direct globe compression to express the nucleus from the capsular bag, these techniques typically use fluid to hydrodissect the nucleus out of the capsular bag into the anterior chamber. Once the nucleus is partly or completely free in the anterior chamber, it can be divided mechanically into smaller pieces that can then be removed through the incision.

Some techniques use an "anterior chamber maintainer", which is a blunt cannula placed into the anterior chamber through a self sealing paracentesis tract (i.e. a stab wound). The other end of the anterior chamber maintainer is connected by tubing to a bottle of balanced salt solution whose height can be varied to control the hydrostatic pressure in the anterior chamber. This maintains the volume in the chamber and forces the nucleus through the incision. (Blumenthal, M).

Amongst the techniques for mechanically dividing the nucleus into smaller pieces are those of Peter Kansas, Eli Khouri and David J. McIntyre. In these techniques, one instrument is inserted between the nucleus and the posterior capsule and a second instrument is placed on the anterior part of the nucleus. Examples of this instrument are a spatula, "vectis" or a "chopping block". The two instruments are manoeuvred toward each other, cleaving the nucleus into two or more pieces. These pieces are small enough to be mechanically expressed or extracted mechanically with forceps or other instruments, through an incision, approximately 6 mm in length, in the cornea or limbus. The softer cortex is then aspirated completely. In most cases, following these techniques an intraocular lens is implanted. This implanted lens usually rests in and is supported by the lens capsule.

The prerequisite for removal of a cataract through a very small incision (<3.2 mm) is a technique to break up the hard nucleus into pieces small enough to be aspirated. One means of accomplishing this is by the use of phacoemulsifier, in which a hollow needle is driven to oscillate longitudinally at extremely high frequencies in the ultra sonic range with minimal amplitude. Charles D. Kelman combined the oscillating tip and evacuation tube into a hollow needle. Direct mechanical impact, like a jackhammer, is a result of this ultrasonic oscillation. The close mechanical contact between the tip and the nucleus, together with the high forward acceleration of the tip and the inertia of the nuclear mass, permits the top to penetrate and destroy nuclear material without just pushing it away. Further destruction of nuclear material is effected by cavitation that occurs at the interface of the fast moving tip and the liquid medium surrounding it. Another force which contributes to the breaking up of the nuclear tissue is the shock wave created by the oscillating tip. The ultrasonic oscillation of the tip is driven with a magnetostrictive transducer or piezoelectric transducer.

Phacoemulsification instruments control the infusion of fluid into the eye and the aspiration of fluid/nuclear fragments from the eye. (Patents by Charles D. Kelman and Anton Banko).

A large number of phacoemulsification techniques have been described, and all share a similar strategy of removal of the nucleus by dividing the lens into multiple pieces, using natural cleavage planes within the lens to mechanically divide the lens. Once divided into small fragments the individual pieces can often be removed by high vacuum force rather than by high phacoemulsification (ultrasonic) energy.

RELEVANT LITERATURE

The following literature describes the prior art:

Blumenthal: Manual ECCE, the Present State of the Art, Klinische Monatsblatter Fur Augenheilkunde 1994; 205: 266–270.

McIntyre, DJ: Phacosection Cataract Surgery. In Steinert, R.F., Fine, I. H., Gimbel H.V. et al, (FDS) Cataract Surgerg, Techniques, Complications and Management: Philadelphia: WB Saunders 1995: 119–123.

Kansas P: Phaco Fracture in Cataract Surgery, Alternative Small Incision Techniques by Rozakis (Ed) Slack 1990: 45–69 and Khouri E: Manual Phacofragmentation, Manual Meeting of Canadian Ophthalmological Society: Jun. 2, 1996 Ottawa.

Vaughn D, Cook R and Asbury T: General Ophthalmology: Lange Medical Publications, 1968

Tippeman R, et al: Clinical Update: Cataract

The American Academy of Ophthalmology, 1996

Preferred Pracitce Pattern: Cataract in the Adult Eye: The American Academy of Ophthalmology, 1996

U.S. Patents:

U.S. Pat. No. 2,850,007 to Lingley
U.S. Pat. No. 3,893,445 to Hofsess
U.S. Pat. No. 3,996,935 to Banko II
U.S. Pat. No. 4,041,947 to Weiss
U.S. Pat. No. 4,282,884 to Boebel
U.S. Pat. No. 4,308,875 to Young
U.S. Pat. No. 4,320,761 to Haddad
U.S. Pat. No. 4,538,611 to Kelman
U.S. Pat. No. 4,570,632 to Woods
U.S. Pat. No. 4,577,629 to Martinez
U.S. Pat. No. 4,590,935 to Ranalli

SUMMARY OF THE INVENTION

The present invention seeks to provide an apparatus for performing surgical procedures on animal anatomy but especially the eye. The invention provides an apparatus for removing the nucleus of the lens of the eye through a small incision (<3.2 mm) using a simple mechanical device, which is manually driven and controlled.

Accordingly, the present invention provides an apparatus to remove tissue comprising:

an outer cannula;

an inner cannula received within the outer cannula, the cannulae being longitudinally movable relative to each other;

an abutment at the end of one cannula to contact the other cannula;

drive means to advance the other cannula to contact the abutment whereby tissue between the other cannula and the abutment is removed.

In a further aspect the invention is an apparatus to remove tissue comprising:

a main body;

an outer cannula extending from a first end of said body;

an abutment at the end of said outer cannula;

an inner cannula received within said outer cannula and reciprocable within said outer cannula;

a slider within said main body to receive said inner cannula;

means to advance said slider and thus said inner cannula;

means to retract said slider and thus said inner cannula; and a suction tube extending from said inner cannula to the exterior of the main body.

BRIEF DESCRIPTION OF THE DRAWINGS

The invention is illustrated in the drawings, in which;

FIGS. 10 through 13C illustrate the use of the apparatus of the invention.

DESCRIPTION OF THE PREFERRED EMBODIMENTS

Figure 1A:
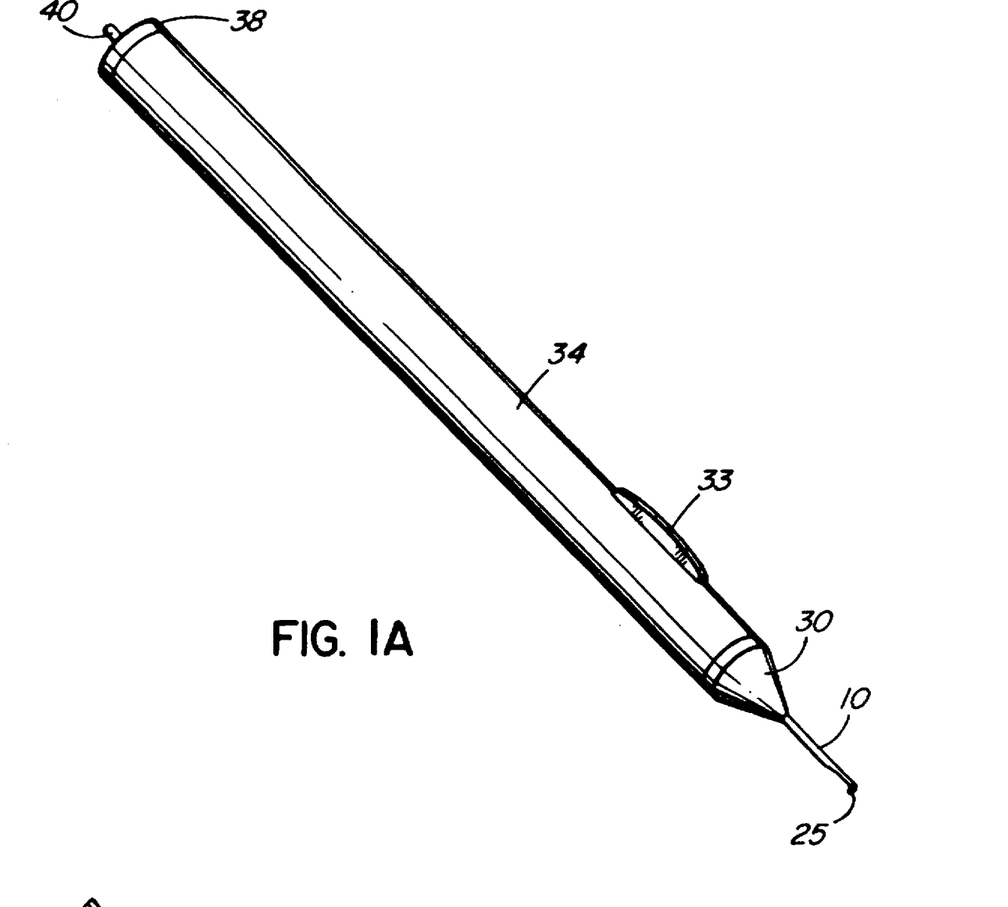
FIG. 1A is a perspective view of a surgical device according to one embodiment of the invention.
Figure 1B:
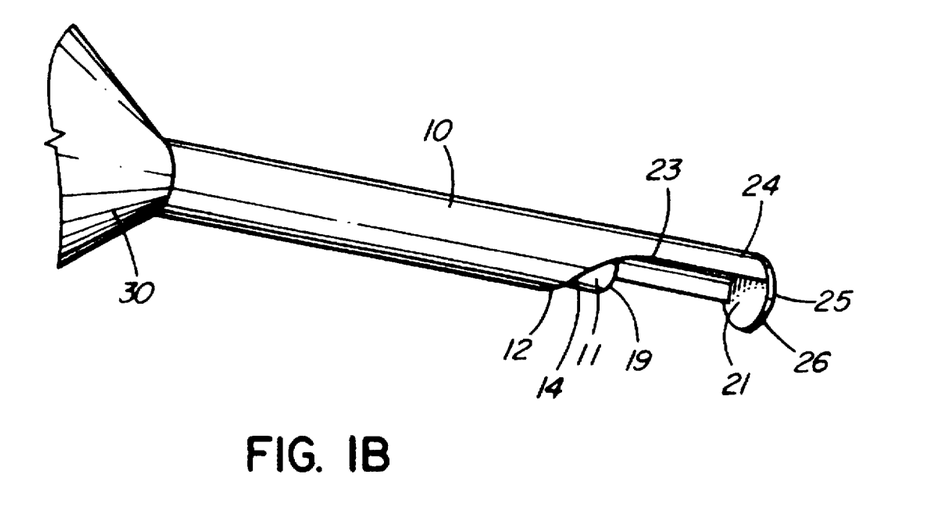
FIG. 1B is an enlarged perspective view of the tip of the device.

FIGS. 1A and 1B show a device for removal of tissue from the eye of a human or an animal. A housing 34 partially houses and supports a pusher 33, which, when depressed by the user, pushes an inner shearing cannula 11 axially inside the outer cannula 10. The end 19 of inner cannula 11 closes tightly against the tip 25 of the outer cannula 10. Tip 25 acts as an anvil or abutment. The cannula 35 is meshed with cannula 11 inside the housing 34 of the device—see FIGS. 2A, 2B and 2C. Cannulae 11 and 35 provide means for aspiration of the tissue when a suction is applied through an attached flexible tube 40. A front end cap 30 of housing 34 provides a support and attachment to outer cannula 10. A rear end cap 38 provides a support to cannula 35 but is not rigidly attached to the cannula 35.

FIG. 1B shows the tip of the device. The figure shows the outer cannula 10 and the inner cannula 11, which is partially advanced. There is a small clearance 14 between the inner cannula 11 and the outer 10, which allows axial movement of the inner cannula 11 inside the outer cannula 10. There is a leading edge 19 to the inner cannula 11. This edge 19 closes tightly against the surface 21 of element 25. Tip 25 has an edge 26 which is placed into the lens of the eye. The connection between tip 25 and the outer cannula is provided by element 24. The back edge 12 of the opening 23 is also shown.

Figure 2A:
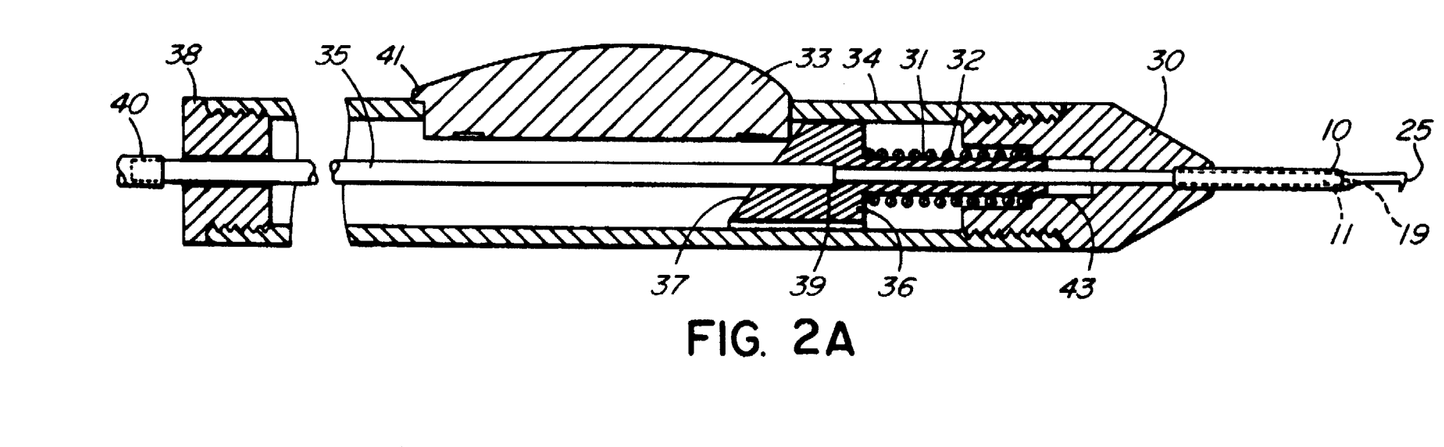
FIG. 2A is a section of one embodiment of the invention.

FIG. 2A shows a driving mechanism for the device. The housing 34 provides a partial housing and support to pusher 33. As pusher 33 is depressed by the user it advances a slider 36 by driving the ramp section 37 of slider 36. The slider 36 is rigidly attached to inner cannula 11 and consequently when the slider 36 moves the inner cannula also moves. As the slider 36 moves forward it compresses a spring 32 which provides a slight counter force to the slider 36 and consequently to the pusher 33 and maintains the ramp 37 in contact with the pusher 33. Spring 32 provides a return mechanism to the advanced inner cannula 11 and returns the pusher 33 to its original position as pressure is removed from pusher 33. Projection 31 of slider 36 supports the spring 32 and is also designed so that a portion of projection 31 is always in front end cap 30. Through the spring 32, with its rigid connections to the slider 36, its connection to the inner cannula and its constant contact with pusher 33, the assembly allows the user to control the amount the inner cannula moves forward or retracts inside the outer cannula 10. The slider 36, in addition to its rigid connection to inner cannula 11, can also provide a location where the inner cannula can increase in diameter to provide a cannula 35 of larger diameter. This aids the aspiration of any fractured material. Cannula 35 is also rigidly connected to slider 36. Therefore distal end cap 38 only provides support to cannula 35 and permits the cannula 35 to move freely axially. Through the advancing mechanism inner cannula 11 can move axially inside outer cannula 10. The leading end 19 of inner cannula 11 meets with an element 25 rigidly attached to the outer cannula 10.

Figure 2B:
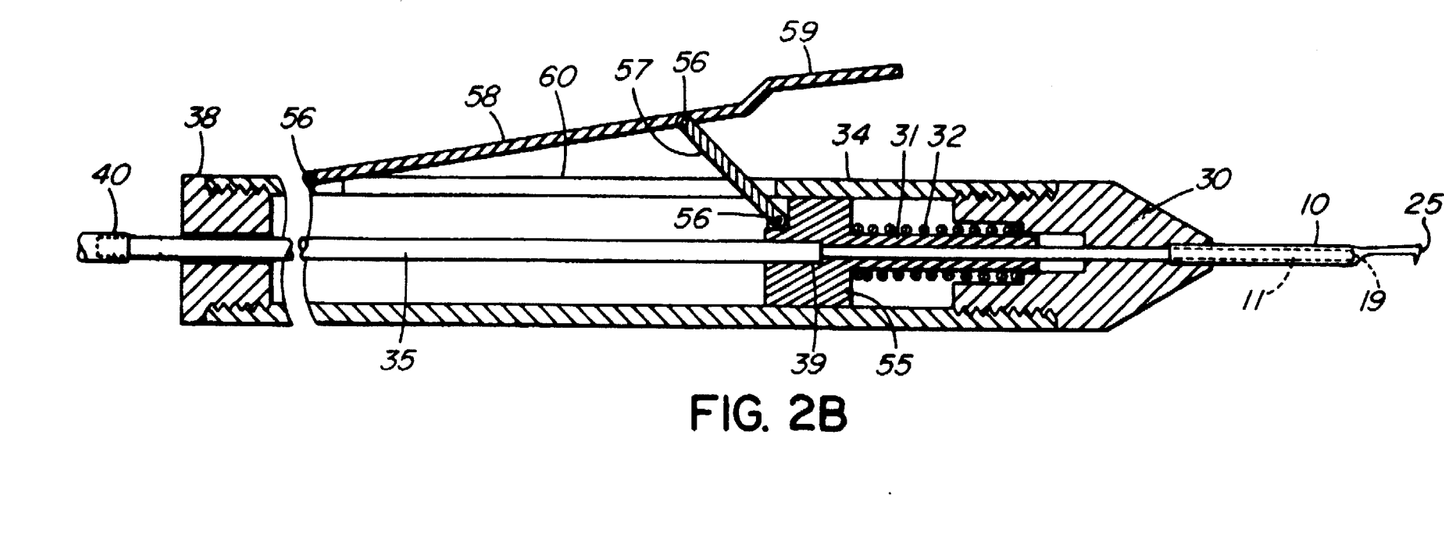
FIGS. 2B and 2C are sections through a further embodiment to the invention.
Figure 2C:
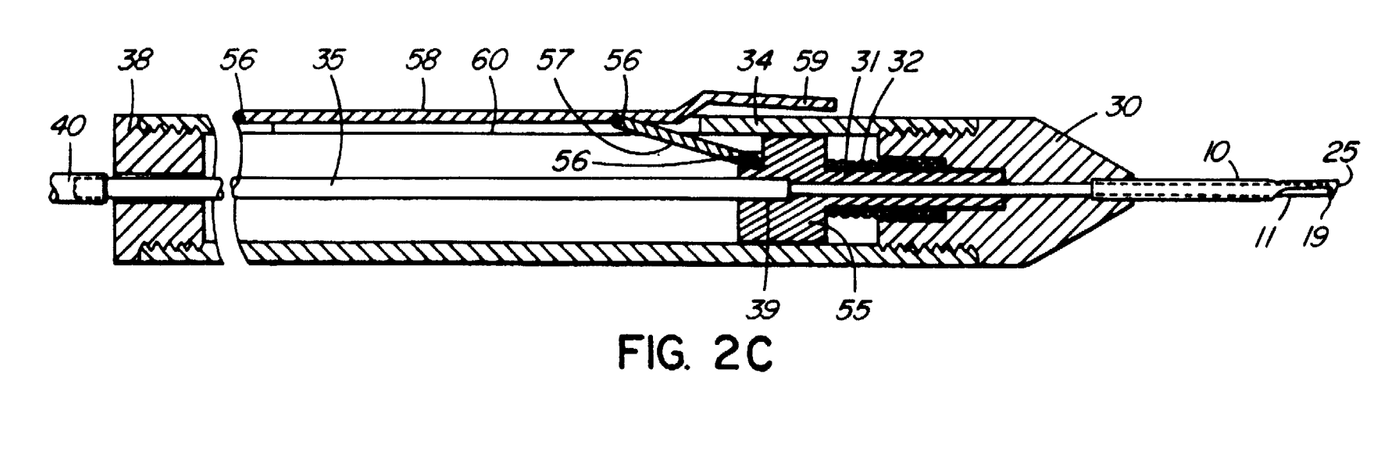

FIGS. 2B, 2C are sections view of a preferred embodiment of the device. In the embodiment of FIGS. 2B and 2C parts common to the embodiment of FIG. 2A have common reference numerals.

The embodiment of FIGS. 2B and 2C differs by the provison of a lever mechanism to replace the pusher 33 of the embodiment of FIG. 2A. A slider 55 replaces slider 36 of the embodiment of 2A. Slider 55 does not have the inclined rear surface 37 of slider 36. Instead slider 55 receives a first pin 56 at one end of a first lever 57. At the second end of lever 57 there is a second pin 56 to attach to a second lever 58 which, again, is pivotally attached by pivot pin 56 to the housing 34. Lever 58 has a leading edge 59 that can be gripped by the user. There is an opening 60 in the body 34 through which first lever stage (i.e. the inner cannula 11 has not yet preadvanced begun to move forward in the outer cannula 10) and the linkage 57,58 is in the opened position. The device in FIG. 2C is in the advanced stage (i.e. the inner cannula now has advanced fully and occupies the complete opening of the outer cannula 11) and the links 57 and 58 have been compressed (advanced). The housing 34 provides a partial housing and support to link 58, 59. As lever 58 is depressed by the user it advances the slider 55 through lever 57. The slider 55 is rigidly attached to inner cannula 11 and consequently, when the slider 55 moves the inner cannula moves accordingly. As the slider 55 moves forward it compresses spring 32 which provides a slight counter force to the moving slider 55 and consequently to the levers 57 and 58 through the pin 56 which connects the lever 57 to the pusher 55. This provides a return mechanism to the advanced inner cannula 11 and also returns the levers 57 and 58 to their rest position as the user removes any pressure applied. The user applies pressure to element 59 of lever 58 and consequently controls the movement of the inner cannula through this lever. The support 31 is designed to remain always in a portion of front end cap 30. Through the spring 32 and its subsequent connections to the pusher 55, and its connection to the inner cannula 11, and its constant contact with levers 57 and 58, the assembly allows the user to control the amount the inner cannula 11 moves forward or retracts inside the outer cannula 10. The slider 55, in addition to its rigid connection to inner cannula 11, can also provide a location where the inner cannula can increase in diameter to cannula 35 of larger diameter. This aids the aspiration of any fractured material. Cannula 35 is also rigidly connected to slider 55. Therefore distal end cap 38 only provides support to cannula 35 and permits the cannula 35 to move freely axially. Through the advancing mechanism inner cannula 11 can move axially inside outer cannula 10. The leading end 19 of inner cannula 11 meets with perpendicular element 25 which is rigidly attached to the outer cannula 10.

FIGS. 3–6 show the tip of the device which provides the means for fracturing the tissue of the lens.

Figure 3:
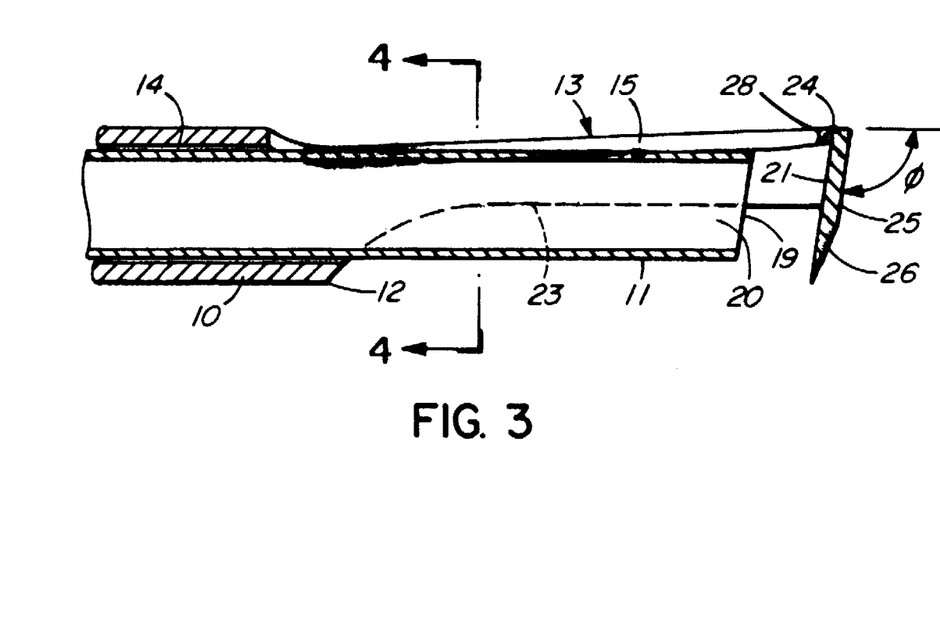
FIG. 3 is an enlarged detail of one embodiment of the invention.

In FIG. 3 the outer cannula 10 allows the inner cannula 11 to travel axially inside. The small gap 14 assists this axial movement by lowering the frictional resistance between the outer and inner cannulas. The outer cannula 10 has 2 openings, one on the bottom 23 and one on the top 13. The bottom opening 23 in the outer cannula 10, along with the tip 25 of the outer cannula, is placed into the tissue which is desired to be fractured and aspirated. The back edge 12 of the opening 23 defines the amount of tissue which can be placed into the opening 23. The taper 26 in the tip 25 lowers the resistance to the placing of the anvil 25 and opening 23 into the tissue. The taper 26 does not come to a completely sharp point, which helps prevent the development of damage to the posterior capsule. Once the opening 23 and the tip 25 are in the tissue to be fractured, inner cannula 11 is advanced inside the outer cannula. End 19 of the inner cannula is at the same angle Ø as the outer cannula's tip 25 which allows a tight closure between the inner cannula 11 and the tip 25. In addition, the tip's inner surface 21 meets the advancing inner cannula's end 19 and completes the closure. The angle Ø of elements 25 and 19 is greater than or equal to 90°. This provides an upward tendency to the tissue being sheared as the inner cannula 11 is being advanced against tip 25. The top opening 13 of the outer cannula 10 provides the user with a possible view port for observing the advancing of the inner cannula's end 19 against inner surface 21. Furthermore, the top opening 13 of outer cannula 10 can add a shearing edge 28 and 15 to the advancing leading tip 19 of the inner cannula 11. The inner cannula 11 can be slightly tapered to the leading edge 19, providing the leading edge 19 with a smaller diameter than the diameter of the inner cannula 11. This assists in the prevention of a plug developing in the lumen 20 of the inner cannula 11 during the aspiration of tissue up the lumen 20.

Figure 4:
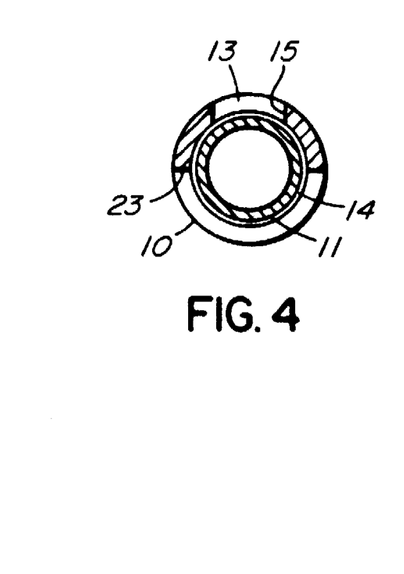
FIG. 4 is a section on the line 4—4 in FIG. 3.

FIG. 4 shows an end view of the top and bottom openings 13 and 23. The inner cannula 11 is inside the outer cannula 10 and the gap 14 between the two cannulas assists the smooth axial motion of the inner cannula inside the outer cannula. FIG. 4 also shows the top opening 13 and inside edge 15 of the top opening.

Figure 5:
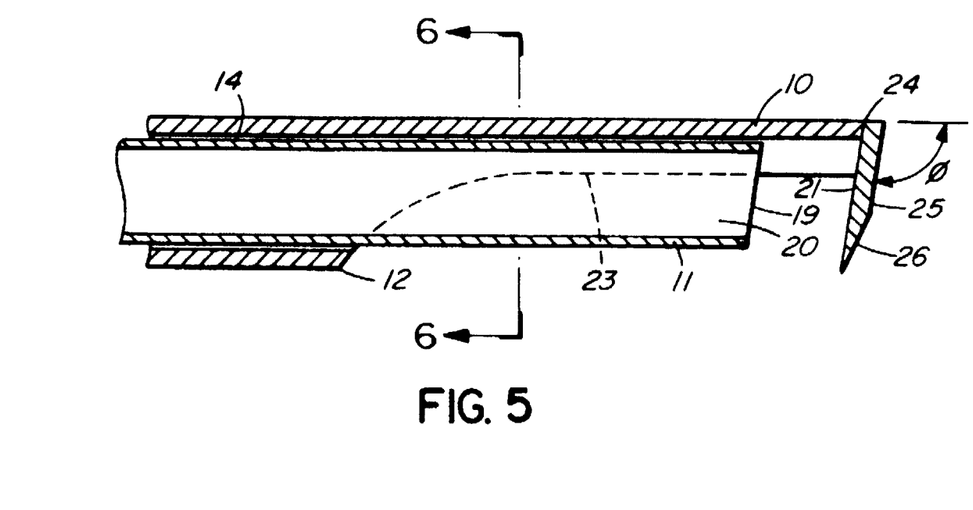
FIG. 5 is a further enlarged detail of a further embodiment.

The embodiment of FIG. 5 is similar to that of FIG. 3 except for the top opening 13 of outer cannula and its edges 15 and 24 in FIG. 3.

Figure 6:
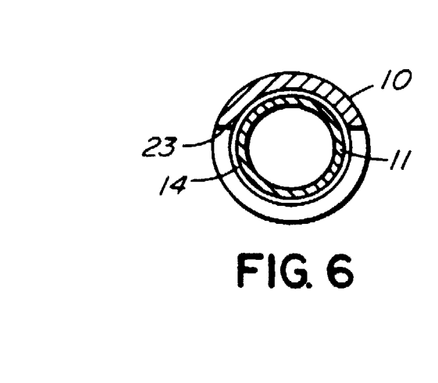
FIG. 6 is a section on the line 6—6 in FIG. 5.

FIG. 6 resembles FIG. 4 except for the top opening 13 of outer cannula 10 in FIG. 4.

Figure 7:
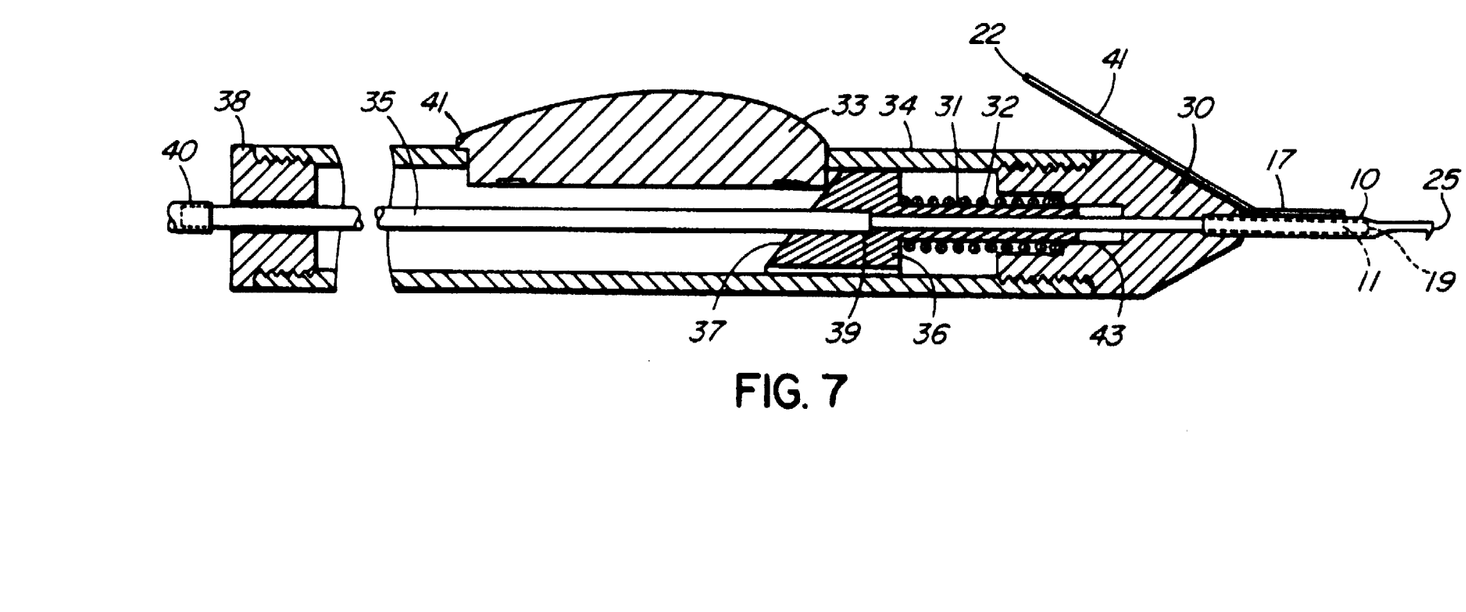
FIG. 7 is a section of a further embodiment.

FIG. 7 closely resembles FIG. 2 but also shows an infusion port 17 and attached tubing 41.

Figure 8:
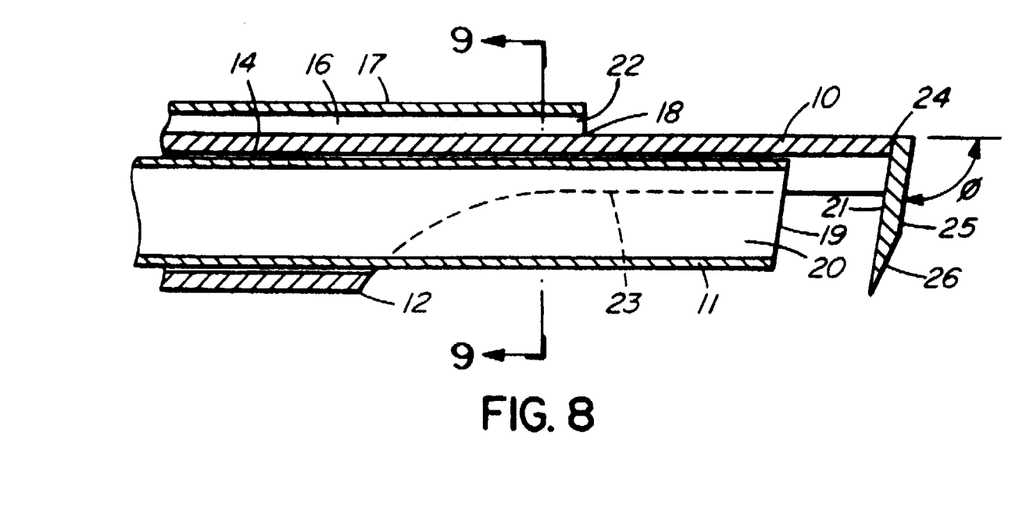
FIG. 8 is an enlarged detail of FIG. 7.

FIG. 8 closely resembles FIG. 5 except the outer cannula 10 of the tip in FIG. 8 has an infusion port attached to it. The infusion port 17 can be a partial to full round cannula and is attached to the outer cannula 10 by element 18 which provides a tight seal so that no leakage occurs between infusion cannula 17 and outer cannula 10. The infusion cannula allows flow 22 through its lumen 16.

Figure 9:
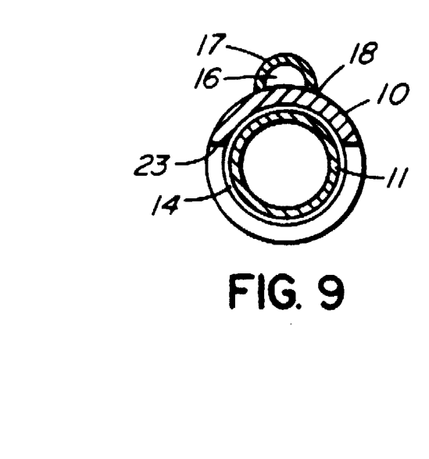
FIG. 9 is a section on the line 9—9 in FIG. 8.

FIG. 9 closely resembles FIG. 6 except the outer cannula 10 of the tip in FIG. 9 has an infusion port 17 attached to it. FIG. 9 shows the infusion cannula 17, its attachment to the outer cannula 11 at element 18, and the infusion lumen 16.

Figure 10:
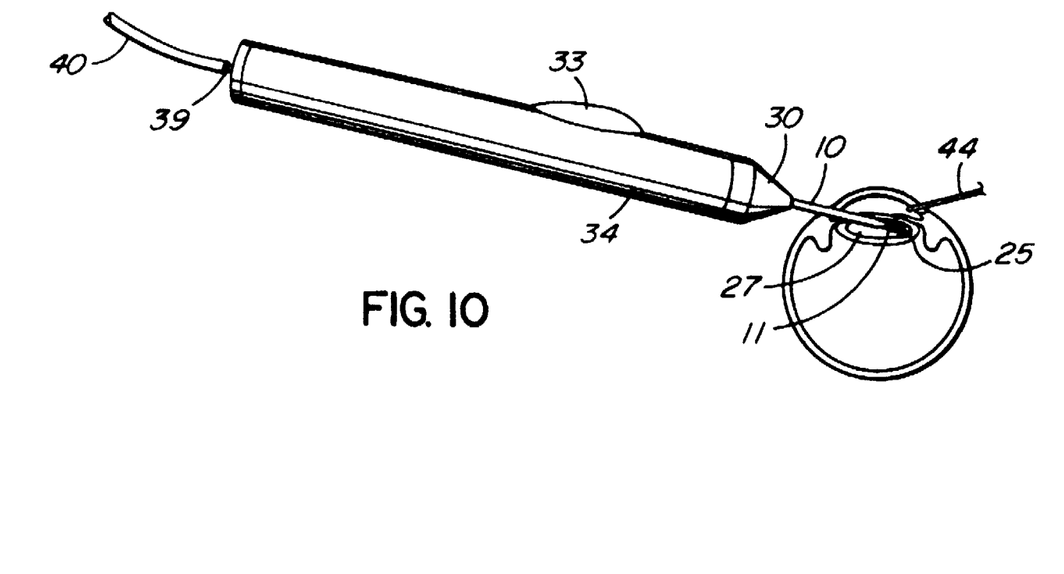

FIG. 10 shows the device in the capsule of an eye and in the process of fracturing and aspiration of nucleus 27 of the lens. The device has a remote infusion port 44. The inner cannula 11 is shown advancing axially in outer cannula 10, pushing the nucleus 27 of the eye against the tip 25.

Figure 11:
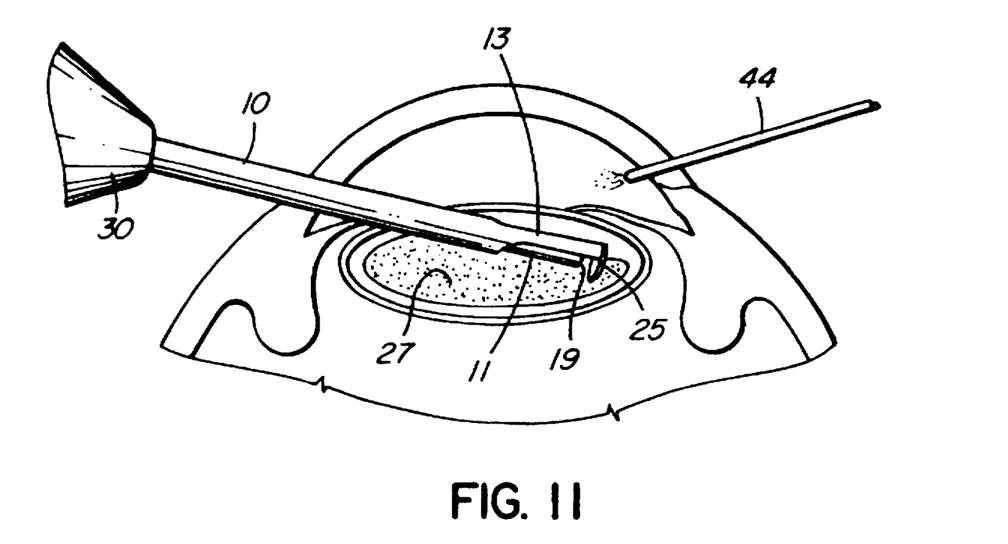

FIG. 11 shows the tip of the device in the capsule of the eye and fracturing the nucleus 27 of the lens of the eye. The nucleus 27 is forced against the tip 25 and by the inner cannula 11 as it is being advanced axially inside the outer cannula 10. Furthermore, the end 19 of the inner cannula 11 fractures the nucleus 27 of the lens against the inner surface 21 of the tip 25. The outer cannula 10 is firmly held in place by the front support 30 of the device. The outer cannula 10 shown is one with an opening 13 in its top.

Figure 12A:
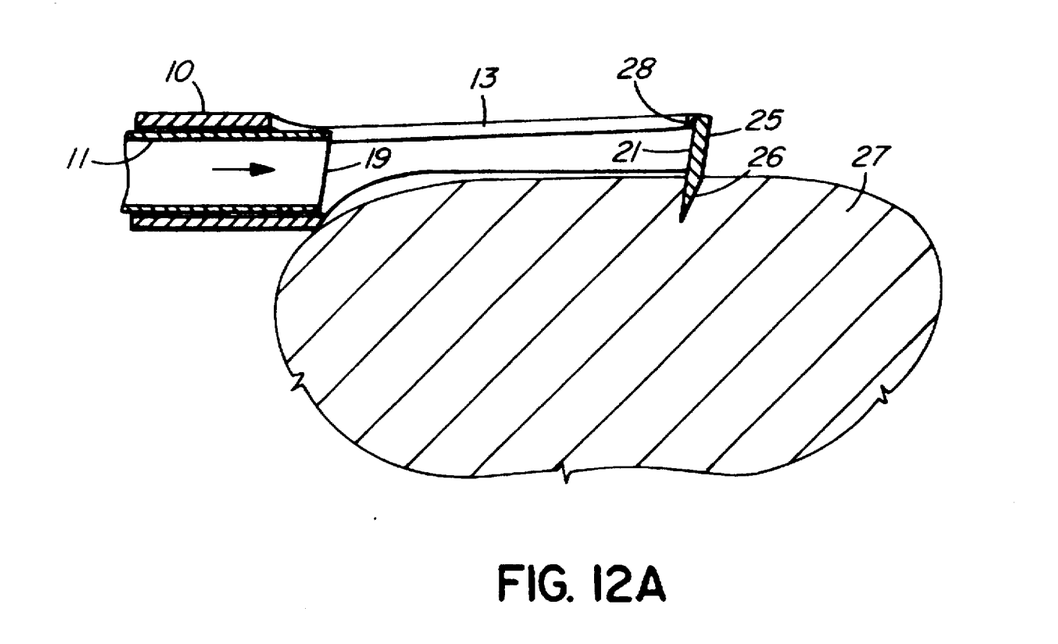
Figure 12B:
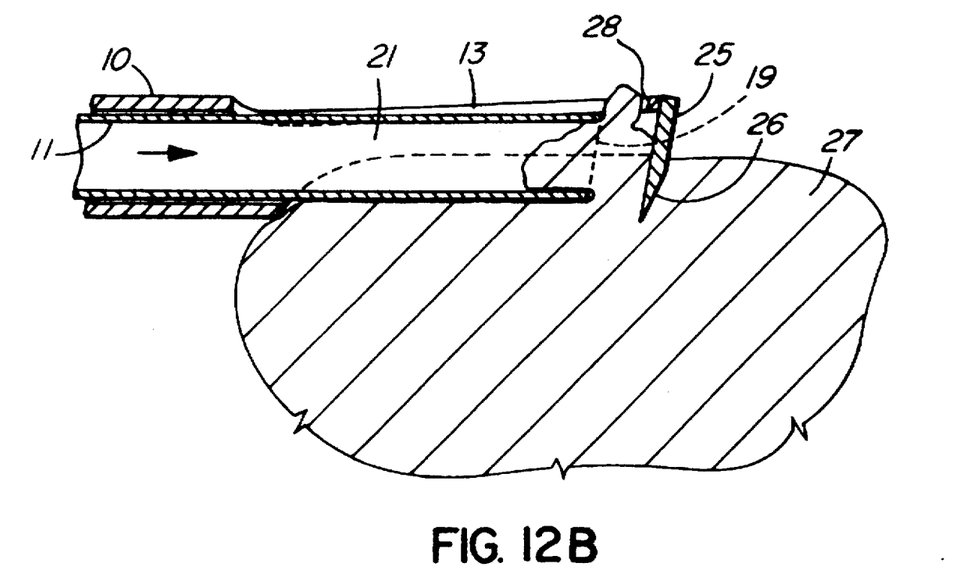
Figure 12C:
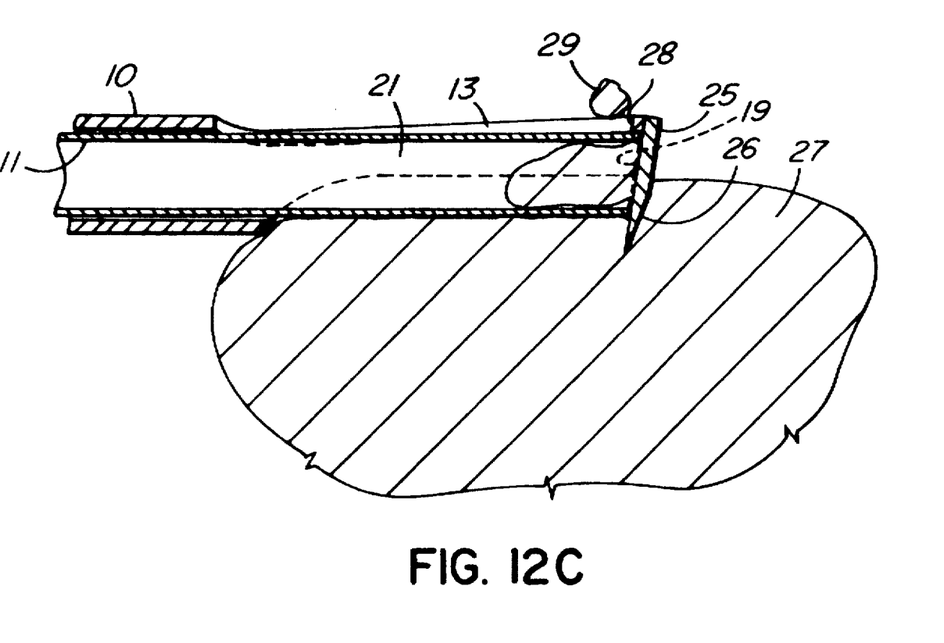

FIGS. 12A to 12C show the edge 19 of inner cannula 11 in various stages of advance and the fracturing of the tissue 27, for example the nucleus of a lens. The figures show the use of the tip from FIG. 3 and FIG. 4. FIG. 12A shows the initial stage of the process with the tip 25 and sharpened portion 26 in the tissue. FIG. 12B shows the edge 19 of inner cannula 11 partially advanced and demonstrates the counter resistance provided by the tip 25 and inner surface 21. The tissue 29 is pushed up in the opening 13 and against edge 28 of the opening 13. FIG. 12C shows the inner cannula's leading edge 19 against the inner surface 21 of the tip 25 and the final fracturing of the tissue. Portions 29 of the fractured nucleus will not immediately pass up the lumen 20 of the inner cannula 11, however these fractured pieces can be easily aspirated during the process of removing the nucleus.

Figure 13A:
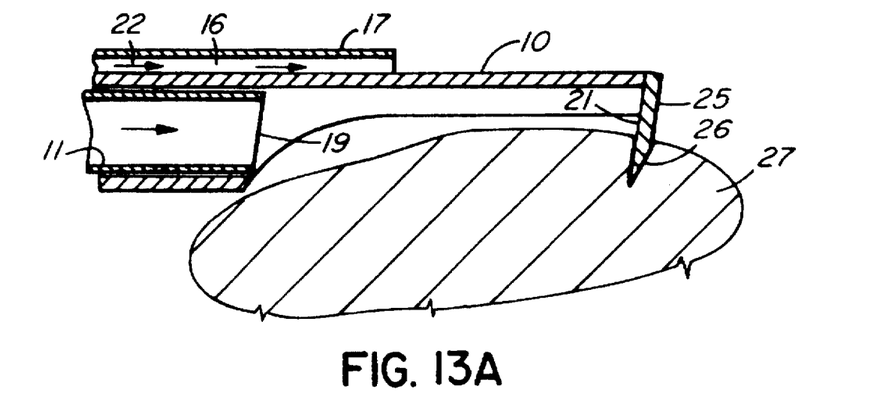
Figure 13B:
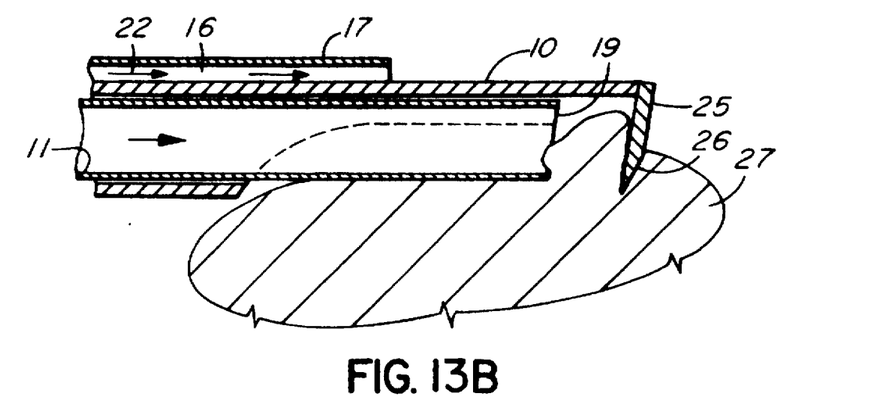
Figure 13C:
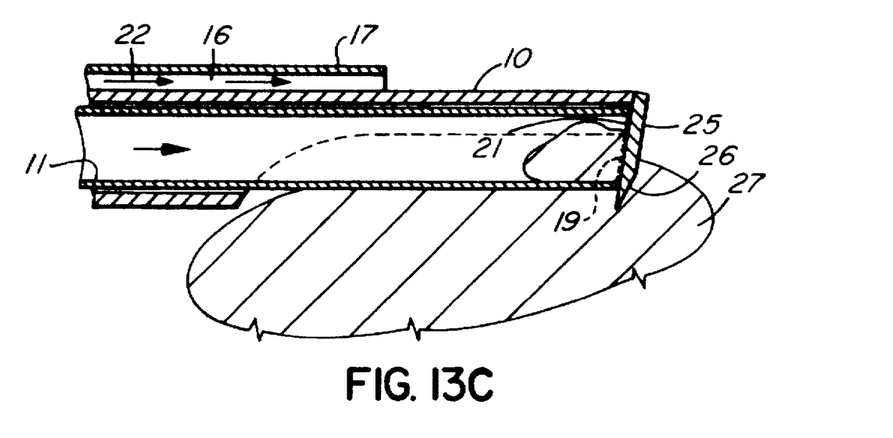

FIGS. 13A to 13C show the edge 19 of inner cannula 11 in various stages of advance and the fracturing of the tissue 27. The series of figures show similar results as demonstrated in FIGS. 12A to 12C, however no opening 13 is present in this embodiment of the device.

The apparatus of the invention is used as follows:

First, using the embodiment of FIGS. 2 to 5 according to FIGS. 10 to 12C, and following the usual preparation and draping of the eye (anaesthetized by a local anaesthetic, a topical anaesthetic or under general anaesthesia) a small blunt cannula, called an interior chamber maintainer (ACM), is placed into the anterior chamber through a self-sealing paracentesis. The end of the anterior chamber maintainer, which is external to the eye, is attached to a bottle of balanced salt solution whose height, relative to the end of the anterior chamber maintainer, can be varied. Fluid from the bottle can flow into the anterior chamber and maintain the pressure to prevent chamber collapse and to facilitate the removal of the lens which has been chopped, fragmented, and macerated into small fragments. This material can be removed from the eye through the apparatus, or by another aspirating cannula.

A second small incision is made into the anterior chamber. It is made through, posterior to, or anterior to the limbus depending on the surgeon's preference. Through this incision an anterior capsulotomy is performed using any of the available instruments for this purpose. Preferably this would be a continuous curvilinear capsulorhexis. Cortical cleaving hydrodissection can be performed by injection of balanced salt solution into the appropriate part of the lens through a small bore cannula, introduced through the second incision. The nucleus can be left within the capsular bag or can be partly or completely dislocated into the anterior chamber by mechanical or hydraulic means. The second wound can then be enlarged, if necessary, to permit entry of the apparatus of the invention into the anterior chamber while maintaining close approximation to the outer cannula of the apparatus to prevent or impede outflow around the apparatus.

The tip of the apparatus engages the anterior lens material if it is soft enough or, if the lens is hard, the apparatus can extend beyond and around the equator of the nucleus. Then, much as a garden hoe can engage the soil, the vertical tip of the outer cannula engages the cortex and/or nucleus, and the inner cannula advances against the tip of the apparatus resulting in the lens material being cut, sheared, fractured and macerated. Most of this fragmented material is driven up the lumen of the inner cannula and the remaining fragmented pieces can be aspirated later in the procedure. This action is repeated and the nucleus of the lens is gradually "gnawed" away and the material in the lumen is forced up the inner cannula by successive strokes. Furthermore, a vacuum applied at the distal end of the apparatus (element 40 in FIG. 2) can assist in the aspiration of the material in the lumen of the inner cannula or of the fragmented material in the anterior chamber. With complete removal of the harder nuclear material the apparatus is removed from the eye and the cortex then aspirated using any one of a variety of available single port single lumen aspirating cannulas.

The use of the embodiment of the invention depicted in FIGS. 7, 8, 9 according to FIGS. 13A, 13B and 13C does not require the insertion of the anterior chamber maintainer as fluid flows through cannula 17 attached to the outer cannula. The operation and removal of the nucleus is otherwise identical to the above description. After the nucleus removal the remaining cortex is aspirated manually using any of the available infusion-aspiration cannulas.

Following complete removal of nucleus and cortex the surgeon has the option of inserting a small ridged intraocular lens through an enlargement of the wound or a foldable lens through the unmodified incision.

The wound is sutured or not sutured depending on the architecture of the incision chosen by the surgeon.

Thus the apparatus of the invention, like phasoemulsification, achieves cataract removal through a small incision, leaving the lens capsule intact except for the anterior capsulotomy opening. The invention achieves this by a simple, manually controlled and driven apparatus.

The invention differs substantially and fundamentally from phacoemulsification and from extracapsular cataract extraction that incorporates the nucleus dividing techniques of Kansas, McIntyre and Khouri.

The apparatus and method of Banko (U.S. Pat. No. 3,732,858) differs fundamentally in that that invention requires the lens to be maintained in the jaws of the device by a suction force applied to the lens. The invention however does not require a constant suction to achieve a shearing of the lens. The cutting elements of Banko rotate about a longitudinal axis, whereas the cutting edges of the invention reciprocate along the axis.

The apparatus described by Wright in U.S. Pat. No. 4,662,869 shears the tissue after the tissue is sucked into the prot of the device. Again the invention does not require this suction to perform the shearing of the lens.

Banko in U.S. Pat. 3,844,279 also requires suction to draw the material to be sheared into the elements of the device. Furthermore, Banko in U.S. Pat. No. 3,996,935 has rotating cutting elements and requires suction to engage and to remove tissue.

Although the present invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

We claim:

1. Apparatus to remove tissue comprising:
   an outer cannula;
   an inner cannula received within the outer cannula, the cannulae being longitudinally movable relative to each other;
   an abutment at the end of one cannula to contact the other cannula, the abutment having a narrowed outer edge to facilitate ingress into tissue to be removed and the abutment substantially covering the end of the other cannula when in contact;
   drive means to advance the other cannula to contact the abutment whereby tissue between the other cannula and the abutment is removed.

2. Apparatus as claimed in claim 1 in which the inner cannula moves and the abutment is on the outer cannula.

3. Apparatus as claimed in claim 1 in which the abutment has a narrowed, but not sharp, outer edge to facilitate ingress into tissue to be removed without cutting supporting tissue, not to be removed.

4. Apparatus as claimed in claim 1 in which the abutment is inclined downwardly rearwardly at an angle of at least 90° to urge shear tissue upwardly as the other cannula advances to contact the abutment.

5. Apparatus as claimed in claim 1 including a vacuum source attached to the apparatus to remove cut tissue.

6. Apparatus as claimed in claim 1 including a support body;
   means to advance the other cannula within the support body; and
   means to retract the other cannula within the support body.

7. Apparatus as claimed in claim 6 in which the means to retract is a spring.

8. Apparatus as claimed in claim 7 in which the spring is a coil spring mounted on said slider to contact an abutment within said support body.

9. Apparatus as claimed in claim 6 in which the support body is a closed tube;
   a vacuum tube attached to said other cannula and extending longitudinally of said support body to an outlet at a distal end of said support body.

10. Apparatus as claimed in claim 1 in which the other cannula is mounted on a slider received within said support body and able to reciprocate within said body; and
    drive means extending through said body to enable a user to advance the slider.

11. Apparatus as claimed in claim 10 in which the slider has an inclined trailing end and in which said drive means is a grip in contact with said trailing end whereby moving the grip downwardly moves said slider forward.

12. Apparatus as claimed in claim 10 in which the drive means comprises a first lever pivoted to said slider;
    a second lever pivoted to said first lever and pivotally mounted at a distal end to said support body, whereby movement of said second lever moves said slider.

13. Apparatus as claimed in claim 1 including a flush cannula to allow ingress of a flushing liquid.

14. Apparatus to remove tissue comprising:
    a main body;
    an outer cannula extending from a first end of said body;
    an abutment at the end of said outer cannula, said abutment having a narrowed outer edge to facilitate ingress into tissue to be removed;
    an inner cannula received within said outer cannula and reciprocable within said outer cannula to contact said abutment, the abutment being dimensioned to substantially cover said inner cannula when in contact;
    a slider within said main body to receive said inner cannula;
    means to advance said slider and thus said inner cannula;
    means to retract said slider and thus said inner cannula; and
    a suction tube extending from said inner cannula to the exterior of the main body.

15. Apparatus as claimed in claim 14 in which the slider has an inclined trailing surface;
    a grip extending through an opening in said main body and contacting said inclined surface whereby movement downwardly of said grip moves the slider forward.

16. Apparatus as claimed in claim 14 in which said drive means comprises a first lever pivoted to said slider;

a second lever pivoted to said first lever and pivotally mounted at a distal end to said support body, whereby movement of said second lever moves said slider.

17. Apparatus as claimed in claim 14 in which the means to retract said slider is a spring.

18. Apparatus as claimed in claim 14 in which the main body is a cylinder having end pieces attached to said cylinder.

* * * * *